United States Patent
McHale et al.

(10) Patent No.: US 9,877,930 B2
(45) Date of Patent: *Jan. 30, 2018

(54) TOPICAL UBIQUINOL ORAL SUPPLEMENT COMPOSITIONS WITH AMORPHOUS CALCIUM PHOSPHATE

(71) Applicant: Premier Dental Products Company, Plymouth Meeting, PA (US)

(72) Inventors: William A. McHale, Collegeville, PA (US); Dale G. Brown, Wharton, TX (US)

(73) Assignee: Premier Dental Products Company, Plymouth Meeting, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/651,064

(22) Filed: Oct. 12, 2012

(65) Prior Publication Data
US 2014/0105937 A1   Apr. 17, 2014

(51) Int. Cl.

| A61K 31/05 | (2006.01) |
|---|---|
| A61K 9/00 | (2006.01) |
| A61P 29/00 | (2006.01) |
| A61P 39/06 | (2006.01) |
| A61K 31/09 | (2006.01) |
| A61Q 11/00 | (2006.01) |
| A61K 8/891 | (2006.01) |
| A61K 8/34 | (2006.01) |
| A61K 47/10 | (2017.01) |
| A61K 31/122 | (2006.01) |
| A61K 33/42 | (2006.01) |

(52) U.S. Cl.
CPC .............. *A61K 31/09* (2013.01); *A61K 8/345* (2013.01); *A61K 8/891* (2013.01); *A61K 9/006* (2013.01); *A61K 9/0014* (2013.01); *A61K 9/0063* (2013.01); *A61K 31/122* (2013.01); *A61K 33/42* (2013.01); *A61K 47/10* (2013.01); *A61Q 11/00* (2013.01)

(58) Field of Classification Search
None
See application file for complete search history.

(56) References Cited

U.S. PATENT DOCUMENTS

| 3,442,842 A | 5/1969 | Bonin |
|---|---|---|
| 4,259,316 A | 3/1981 | Nakashima et al. |
| 4,296,096 A | 10/1981 | Pierce |
| 4,647,451 A | 3/1987 | Piechota |
| 4,652,441 A | 3/1987 | Okada et al. |
| 4,711,782 A | 12/1987 | Okada et al. |
| 4,911,927 A | 3/1990 | Hill et al. |
| 4,942,034 A | 7/1990 | Hill et al. |
| 5,009,881 A | 4/1991 | Hill et al. |
| 5,032,387 A | 7/1991 | Hill et al. |
| 5,037,639 A | 8/1991 | Tung |
| 5,057,306 A | 10/1991 | Hill et al. |
| 5,057,307 A | 10/1991 | Hill et al. |
| 5,057,309 A | 10/1991 | Hill et al. |
| 5,098,711 A | 3/1992 | Hill et al. |
| 5,165,913 A | 11/1992 | Hill et al. |
| 5,268,167 A | 12/1993 | Tung |
| 5,427,768 A | 6/1995 | Tung |
| 5,437,857 A * | 8/1995 | Tung .............................. 424/52 |
| 5,460,803 A | 10/1995 | Tung |
| 5,538,667 A | 7/1996 | Hill et al. |
| 5,562,895 A | 10/1996 | Tung |
| 5,614,175 A | 3/1997 | Winston et al. |
| 5,645,841 A | 7/1997 | Hill et al. |
| 5,651,959 A | 7/1997 | Hill et al. |
| 5,665,374 A | 9/1997 | Hill et al. |
| 5,665,382 A | 9/1997 | Grinstaff et al. |
| 5,711,935 A | 1/1998 | Hill et al. |
| 5,925,595 A | 7/1999 | Seitz |

(Continued)

FOREIGN PATENT DOCUMENTS

| CN | 1093058 A | 10/1994 |
|---|---|---|
| CN | 1190342 A | 8/1998 |

(Continued)

OTHER PUBLICATIONS

Search Report dated Jun. 2, 2016 which issued in the corresponding European Patent Application No. 13845393.1.
Ernster, L., et al., "Ubiquinol: an endogenous antioxidant in aerobic organisms", Clinical Investigator, vol. 71, pp. S60-S65, 1993.
Nizet, V., et al., "Cathelicidins and Innate Defense Against Invasive Bacterial Infection", Scandinavian Journal of Infectious Diseases, vol. 35, No. 9, pp. 670-676, 2003.
Øgaard, B., et al., "Relative cariostatic effects of KOH-soluble and KOH-insoluble fluoride in situ", J. Dent Res, vol. 69, pp. 1505-1507, 1990.
Øgaard, B., "CaF2 Formation: Cariostatic Properties and Factors of Enhancing the Effects", Caries Res., vol. 35 (Suppl 1), No. 11, pp. 40-44, 2001.

(Continued)

*Primary Examiner* — Bethany P Barham
*Assistant Examiner* — Dominic Lazaro
(74) *Attorney, Agent, or Firm* — Cozen O'Connor

(57) ABSTRACT

Topical, UBIQUINOL, adjunctive, supplement compositions, containing amorphous calcium phosphate fluoride (ACPF), useful in: reducing oxidative stress, relieving oral discomfort and dry mouth, and remineralizing hydroxyapatite; comprising: UBIQUINOL in an aqueous-free emulsion that also contains: a stabilizing composition for UBIQUINOL, spilanthes extract, a trans-oral mucosal, absorption facilitator and ACPF; wherein: the emulsion forms a mucoadhesive gel in the presence of saliva that undergoes gradual saliva dissolution effecting passive diffusion of the UBIQUINOL supplement and the spilanthes extract into the oral mucosa, and remineralizing of tooth surfaces with ACPF; resulting in: adjunctively increasing UBIQUINOL levels, reducing oxidative stress, regulating immune response, relieving oral discomfort and dry mouth, and remineralizing tooth surfaces.

18 Claims, No Drawings

(56) References Cited

U.S. PATENT DOCUMENTS

| | | | |
|---|---|---|---|
| 5,952,317 A | 9/1999 | Deluca et al. | |
| 6,054,119 A * | 4/2000 | Hurme | A23G 4/064 424/435 |
| 6,086,373 A | 7/2000 | Schiff et al. | |
| 6,159,449 A | 12/2000 | Winston et al. | |
| 6,184,255 B1 | 2/2001 | Tatsumasa et al. | |
| 6,441,050 B1 * | 8/2002 | Chopra | 514/675 |
| 6,534,091 B1 | 3/2003 | Garces Garces et al. | |
| 6,545,077 B2 | 4/2003 | Hill et al. | |
| 6,569,408 B1 | 5/2003 | Yue et al. | |
| 6,575,176 B1 | 6/2003 | Hill et al. | |
| 6,740,338 B1 * | 5/2004 | Chopra | 424/456 |
| 7,017,591 B2 | 3/2006 | Brown et al. | |
| 7,025,986 B2 | 4/2006 | Brown et al. | |
| 7,152,611 B2 | 12/2006 | Brown et al. | |
| 7,303,921 B2 | 12/2007 | Littarru et al. | |
| 7,897,169 B2 | 3/2011 | Ueda et al. | |
| 2002/0090398 A1 | 7/2002 | Dunn et al. | |
| 2003/0165442 A1 | 9/2003 | Baig et al. | |
| 2003/0198604 A1 | 10/2003 | Lawlor | |
| 2004/0057908 A1 | 3/2004 | Bowen | |
| 2004/0126335 A1 | 7/2004 | Faller et al. | |
| 2004/0258634 A1 * | 12/2004 | Cazor et al. | 424/52 |
| 2005/0196440 A1 | 9/2005 | Masters et al. | |
| 2006/0093558 A1 * | 5/2006 | Lin et al. | 424/47 |
| 2006/0120980 A1 | 6/2006 | Eberl | |
| 2006/0177384 A1 | 8/2006 | Brown | |
| 2006/0286046 A1 | 12/2006 | Haber | |
| 2007/0025928 A1 | 2/2007 | Glandorf et al. | |
| 2007/0190090 A1 * | 8/2007 | Brown | 424/401 |
| 2008/0039434 A1 | 2/2008 | Colli | |
| 2008/0044454 A1 | 2/2008 | Yang et al. | |
| 2008/0050408 A1 | 2/2008 | Hayman et al. | |
| 2008/0069781 A1 | 3/2008 | Neuberger | |
| 2008/0095719 A1 * | 4/2008 | Herrmann et al. | 424/48 |
| 2008/0152598 A1 | 6/2008 | Basic | |
| 2008/0152599 A1 | 6/2008 | Brignoli et al. | |
| 2008/0175918 A1 | 7/2008 | Laulicht | |
| 2008/0226710 A1 * | 9/2008 | Fantuzzi | 424/456 |
| 2008/0247973 A1 | 10/2008 | Baig et al. | |
| 2008/0286214 A1 | 11/2008 | Brown et al. | |
| 2008/0295960 A1 | 12/2008 | Schalau et al. | |
| 2009/0042161 A1 | 2/2009 | Jodaikin et al. | |
| 2009/0087501 A1 | 4/2009 | Cummins | |
| 2009/0188520 A1 | 7/2009 | Brown | |
| 2009/0232752 A1 * | 9/2009 | Carson et al. | 424/59 |
| 2009/0280078 A1 | 11/2009 | Belfer | |
| 2010/0135918 A1 | 6/2010 | Kim et al. | |
| 2010/0330003 A1 | 12/2010 | Robinson et al. | |
| 2011/0014136 A1 * | 1/2011 | Kohli | A61K 8/365 424/52 |
| 2011/0104052 A1 | 5/2011 | Barnett et al. | |
| 2011/0118217 A1 | 5/2011 | Gudmundsson et al. | |
| 2012/0021031 A1 | 1/2012 | Chopra et al. | |
| 2012/0064136 A1 | 3/2012 | Baker et al. | |
| 2012/0129135 A1 | 5/2012 | Yang et al. | |
| 2012/0171128 A1 | 7/2012 | Ramirez | |
| 2012/0207686 A1 | 8/2012 | Fruge et al. | |
| 2012/0245080 A1 | 9/2012 | Goolsbee et al. | |
| 2013/0344120 A1 | 12/2013 | Scott et al. | |

FOREIGN PATENT DOCUMENTS

| | | |
|---|---|---|
| CN | 101056606 A | 10/2007 |
| EP | 0559262 A1 | 9/1993 |
| EP | 0868903 A2 | 10/1998 |
| JP | H11506769 A | 6/1999 |
| JP | H11243910 A | 9/1999 |
| JP | 2004535453 A | 11/2004 |
| JP | 2008534629 A | 8/2008 |
| WO | 1995011746 A1 | 5/1995 |
| WO | 1996039116 A | 12/1996 |
| WO | WO 9639116 A1 * | 12/1996 |
| WO | 2001026577 A1 | 4/2001 |
| WO | 2001068046 A2 | 9/2001 |
| WO | 2003068173 A1 | 8/2003 |
| WO | 2006105615 A1 | 10/2006 |
| WO | 2007036802 | 4/2007 |
| WO | 2007092811 A2 | 8/2007 |
| WO | 2007099398 A1 | 9/2007 |
| WO | 2008041055 A1 | 4/2008 |
| WO | 2008047882 A1 | 4/2008 |
| WO | 2009080022 A1 | 7/2009 |
| WO | 2009153634 A | 12/2009 |
| WO | 2010010394 A2 | 1/2010 |
| WO | 2013039906 A1 | 3/2013 |
| WO | 2013095366 A1 | 6/2013 |
| WO | 2014001132 A1 | 1/2014 |

OTHER PUBLICATIONS

Oral Health: Different Ages/Different Stages: Birth to 12 Years, Ontario, Mar. 2009, pp. 1-24.

Park, K.S., et al., "The short vitamin D receptor is associated with increased risk for generalized aggressive periodontitis", Journal of Clinical Periodontology, vol. 33, No. 8, pp. 524-528, 2006.

Pendrys, D.G., "Risk of Enamel Fluorosis in Nonfluoridated and Optimally Fluoridated Populations: Considerations for be Dental Professional", Journal of the American Dental Association, vol. 131, No. 6, pp. 746-755, 2000.

Ripa, L.W., "A critique of topical fluoride methods (dentifrices, mouthrinses, operator-, and self-applied gels) in an era of decreased caries and increased fluorosis prevalence", J Public Health Dent., Winter, vol. 51, No. 1, pp. 23-41, 1991.

Rolla, G., et al., "Concentration of fluoride in plaque a possible mechanism", Scand. J. Dent. Res., vol. 85, pp. 149-151, 1977.

Rose, R.K., et al., "A quantitative study of calcium binding and aggregation in selected oral bacteria", J Dent Res, vol. 72, pp. 78-84, 1993.

Roveri, N., et al., "Surface Enamel Remineralization: Biomimetic Apatite Nanocrystals and Fluoride Ions Different Effects", Journal of Nanomaterials, vol. 2009, Article ID 746383, 9 pages.

Schaeken, M.J., et al., "Effects of fluoride and chlorhexidine on the microflora of dental root surfaces and the progression of root-surface caries", J Dent Res, vol. 70, No. 2, pp. 150-153, 1991.

Schemehorn, B.R., et al., "Remineralization by Fluoride Enhanced with Calcium and Phosphate Ingredients", Indiana University School of Dentistry, The British Library, Enamelon, Inc.

Schemehorn, B.R., et al., "Comparision of Fluoride Uptake into Tooth Enamel from Two Fluoride Varnishes Containing Different Calcium Phosphate Sources", ACP Technology, The Journal of Clinical Dentistry, vol. XXII, No. 2, pp. 51-54, 2011.

Schmelzer, C., et al., "In vitro effects of the reduced form of coenzyme Q10 on secretion levels of TNF-α and chemokines in response to LPS in the human monocytic cell line THP-1," Journal of Clinical Biochemistry and Nutrition, vol. 44, No. 1, pp. 62-66, 2009.

Schreiber, C.T., et al., "Effects of rinses with an acidic calcium phosphate solution on fluoride uptake, caries and in situ plaque pH in rats", J Dent Res, vol. 67, pp. 959-963, 1988.

Stookey, G.K., "Critical evaluation of the composition and use of topical fluorides", J Dent Res, vol. 69 (Spec Iss), pp. 805-812, 1990.

Sun, J., "Vitamin D and mucosal immune function", Current Opinion in Gastroenterology, vol. 26, No. 6, pp. 591-594, Nov. 2010.

Tan, H.P., et al., "A randomized trial on root caries prevention in elders", J Dent Res, vol. 89, No. 10, pp. 1086-1090, 2010.

Tang, P.H., et al., "HPLC Analysis of Reduced and Oxidized Coenzyme Q10 in Human Plasma", Clinical Chemistry, vol. 47, No. 2, pp. 256-265, 2001.

Ten Cate, J.M., "Review on Fluoride with special emphasis on calcium fluoride mechanisms in caries prevention", Eur. J. Oral Sci., vol. 105 (5 pt 2), pp. 461-465, Oct. 1997.

Ten Cate, J.M., "Current Concepts on the Theories of the Mechanism of Action of Fluoride", Academic Centre for Dentistry Amsterdam (ACTA), Department of Cariology, Endodontology Pedodontology, Amsterdam, The Netherlands, ACTA Odontol Scand, vol. 57, pp. 325-329, 1999.

(56) References Cited

OTHER PUBLICATIONS

Tewari, A., et al., "Comparative evaluation of the role of NaF, APF, and Duraphat topical fluoride applications in the prevention of dental caries: a 2 1/2 year study", J Indian Soc Pedod Prev Dent, vol. 8, pp. 28-36, 1990.
Thies, C., "A Survey of Microencapsulation Processes", Washington University, St. Louis, Missouri.
Tung, M.S., et al., "Dental applications of amorphous calcium phosphates", J. Clin Dent, vol. 10, pp. 1-6, 1999.
Tung, M.S., et al., "DE2, Amorphous Calcium Phosphates for Tooth Mineralization", Compendium, vol. 25, No. 9 (Suppl 1), pp. 9-13, Sep. 2004.
Turner, D., et al., "The Interaction of Stannous Fluoride with Synthetic Hydroxyapatite: Modeling the Anticaries Effect", Ceramics—Silikaty, vol. 57, No. 1, pp. 1-6, 2013.
Vaikuntam, J., "Fluoride varnishes: should we be using them?", Pediatr Dent, vol. 22, pp. 513-516, 2000.
Vieth, R. et al. "Efficacy and safety of vitamin D3 intake exceeding the lowest observed adverse effect level", Am J Clin Nutr, vol. 73, No. 2, pp. 288-294, Feb. 2001.
Vogel, G.L., et al., "Salivary fluoride from fluoride dentifrices or rinses after use of a calcium pre-rinse or calcium dentifrice", Caries Res., vol. 40, pp. 449-454, 2006.
Vogel, G.L., et al., "Calcium Pre-Rinse Greatly Increases Overnight Salivary Fluoride after a 228 ppm Fluoride Rinse", Caries Res., vol. 42, No. 5, pp. 401-404, Sep. 2008.
Vogel, G.L., et al., "Ca Pre-Rinse Greatly Increases Plaque and Plaque F fluid F", J. Dent. Res., vol. 87, No. 5, pp. 466-469, May 2008.
Vogel, G.L., et al., "No Calcium-Fluoride-Like Deposits Detected in Plaque shortly after a Sodium Fluoride Mouthrinse", Caries Res., vol. 44, No. 2, pp. 108-115, 2010.
Walton, J.G., et al., "Textbook of Dental Pharmacology and Therapeutics", Oxford University Press 1994, pp. 149 and 154.
Wang, X.L., et al., "Cosupplementation with vitamin E and coenzyme Q10 reduces circulating markers of inflammation in baboons1-3", Am. J. Clin. Nutr., vol. 80, No. 3, pp. 649-655, Sep. 2004.
Wang, C., et al., "Association Between Vitamin D Receptor Gene Polymorphisms and Severe Chronic Periodontitis in a Chinese Population", Journal of Periodontology, vol. 80, No. 4, pp. 603-608, 2009.
Warren, J.J., et al., "A review of fluoride dentifrice related to dental fluorosis", Pediatr. Dent., vol. 21, No. pp. 265-271, Jul.-Aug 1999.
Wilkinson, E.G., et al., "Bioenergetics in clinical medicine. II. Adjunctive treatment with coenzyme Q10 in periodontal therapy", Res. Com. Chem. ath. Pharm. vol. 12, No. 1, p. 111-123, 1975.
Wilkinson, E.G., et al., "Bioenergetics in clinical medicine. VI. Adjunctive treatment of periodontal disease with menzyme Q10", Res. Com. Chem. Path. Pharm., vol. 14, No. 4, pp. 715-719, 1976.
Wu, L.C., et al., "Anti-inflammatory effect of spilanthol from Spilanthes acmelia on murine macrophage by down-regulating LPS-induced inflammatory mediators", J. Agric. Food Chem., vol. 56, No. 7, pp. 2341-2349, Apr. 9, 2008 (Apr. 9, 2008), Abstract.
Xu, H.H.U., et al., "Strong Nanocomposites with Ca PO4, and F Release for Caries Inhibition", J. Dent Res, vol. 89, No. 1, pp. 19-28, 2010.
Zero, D.T., "Dentifrices mouthwashes, and remineralization/caries arrestment strategies", BMC Oral Health, vol. 6 (Suppl 1), No. 59, pp. 1-13.
Attin, T., et al., "Deposition of fluoride on enamel surfaces released from varnishes is limited to vicinity of fluoridation site", Clin Oral Investig, vol. 11, pp. 83-88, 2007.
Barry, R., "The Power of Ubiquinol", The Key to Energy, Vitality, and a Healthy Heart, Chapter 4, Studies and Research: The Health Benefits of Ubiquinol, pp. 21-25, 2010.
Bashutski, J.D., et al., "The Impact of Vitamin D Status on Periodontal Surgery Outcomes ", J. Dent. Res., vol. 90, No. 8, pp. 1007-1012, 2011.
Beltran-Aguilar, E.D., et al., "Fluoride varnishes: A review of their clinical use, cariostatic mechanism, efficacy and safety", JADA, vol. 131, pp. 589-594, 2000.
Caslayska, V., et al., "CaF2 in Enamel Biopsies 6 Weeks and 18 Months after Fluoride Treatment", Caries Res, vol. 25, pp. 21-26, 1991.
Chantal, J., et al., "The coming of age of 1,25-dihydroxyvitamin D3 analogs as immunomodulatory agents", Trends Mol Med., vol. 8, No. 4, pp. 174-179, 2002.
Charig, A., et al., "CE3 Enamel Mineralization by Calcium-containing Bicarbonate Toothpastes: Assessment by Various Techniques", Compendium, vol. 25, No. 9 (Suppl 1), pp. 15-31, Sep. 2004.
Chow, L.C., et al., "Apatitic fluoride increase in enamel from a topical treatment involving intermediate CaHPO4.2H2O formation, an in vivo study", Caries Res., vol. 15, pp. 369-376, 1981.
Christoffersen, J., et al., "Kinetics of dissolution and growth of calcium fluoride and effects of phosphate", Acta Odontol Scand, vol. 46, No. 6, pp. 325-336, 1988.
Crall, J.J. et al., "Enamel fluoride retention after DCPD and APF application and prolonged exposure to fluoride in vitor", J. Dent Res, vol. 65, No. 3, pp. 387-389, 1986.
Cruz, R., et al., "Uptake of KOH-soluble and KOH-insoluble fluoride in sound human enamel after topical application of a fluoride varnish (Duraphat) or a neutral 2% NaF solution in vitro", Scand J Dent Res., vol. 100, No. 3, pp. 154-158, 1992.
Diamond, G., et al., "Host defense peptides in the oral cavity and the lung: similarities and differences", J. Dent. Res., vol. 87, No. 10, pp. 915-927, 2008.
Dietrich, T., et al., Association between serum concentrations of 25-hydroxyvitamin D and gingival inflammation1'2'3', Am. J. Clin. Nutr., vol. 82, No. 3, pp. 575-580, 2005.
Dijkman, A.G., et al., "In vivo investigation on the fluoride content in and on human enamel after topical applications", Caries Res., vol. 17, pp. 392-402, 1983.
Dimeloe S. et al., "Regulatory T cells, inflammation and the allergic response—The role of glucocorticoids and Vitamin D", Journal of Steroid Biochemistry & Molecular Biology, vol. 120, Issues 2-3, pp. 86-95, 2010.
Dixon, D., et al., "Calcium and vitamin D use among adults in periodontal disease maintenance programmes", British Dental Journal, vol. 206, No. 12, pp. 627-631, 2009.
Dudev, T., et al., "Monodentate versus bidentate carboxylate binding in magnesium and calcium proteins: what are the basic principles?", J. Phys. Chem. B., vol. 108, pp. 4546-4557, 2004.
Featherstone, J.D., "Prevention and reversal of dental caries: role of low level fluoride", Community Dent Oral Epidemiol, vol. 27, pp. 31-40, 1999.
Featherstone, J.D.B., "The Science and Practice of Caries Prevention", Journal of the American Dental Association, vol. 131, pp. 887-899, 2000.
Folkers, K., "A critique of 25 years of research which culminated in the successful therapy of periodontal disease with coenzyme Q10", J. Dent. Health, vol. 42, pp. 258-263, 1992.
Garcia, M., et al., "One-Year Effects of Vitamin D and Calcium Supplementation on Chronic Periodontitis", Journal of Periodontology, vol. 82, No. 1, pp. 25-32, 2011.
Gombart, A.F., "The vitamin D-antimicrobial peptide pathway and its role in protection against infection", Future Microbiology, vol. 4, No. 9, pp. 1151-1165, 2009.
Hanioka, T., et al., "Therapy with Coenzyme Q10 for Patients with Periodontal Disease: 2. Effect of Coenzyme Q10 on the Immune System", Journal of Dental Health, vol. 43, pp. 667-672, 1993.
Hanioka, et al., "Effect of Topical Application of Coenzyme Q10 on Adult Periodontitis", Malec. Aspects of Med., vol. 85 (Supplement), pp. S241-S248, 1994.
Hansdottir, S., et al., "Vitamin D Decreases Respiratory Syncytial Virus Induction of NF-κB—Linked Chemokines and Cytokines in Airway Epithelium While Maintaining the Antiviral State", The Journal of Immunology, vol. 184, No. 2, pp. 365-974, 2010.
Helfenstein, U., et al., "Fluoride varnishes (Duraphat): A meta-analysis." Community Dent Oral Eipdemiol, vol. 22, pp. 1-5, 1994.

(56) References Cited

OTHER PUBLICATIONS

Hewison, M., "Review: Vitamin D and the intracrinology of innate immunity", Molecular and Cellular Endocrinology, vol. 321, No. 2, pp. 103-111, 2010.
Holick, M.F., "Vitamin D Deficiency", New England Journal of Medicine, vol. 357, pp. 266-281, 2007.
Holick, M.F., "Vitamin D Status: Measurement, Interpretation, and Clinical Application", Annals of Epidemiology, vol. 19, No. 2, pp. 73-78, 2009.
Hong, Y.C., "Enhanced fluoride uptake from mouthrinses", J Dent Res., vol. 64, pp. 82-84, 1985.
International Search Report and Written Opinion dated Oct. 12, 2012 which issued in International Patent Application No. PCT/US2013/064358.
International Search Report and Written Opinion dated Apr. 21, 2014 which issued in International Patent Application No. PCT/US2013/064504.
International Search Report and Written Opinion dated Jul. 2, 2015 which issued in International Patent Application No. PCT/US2015/025375.
International Search Report and Written Opinion dated Jul. 10, 2015 which issued in International Patent Application No. PCT/US2015/025385.
International Search Report and Written Opinion dated Jul. 2, 2015 which issued in International Patent Application No. PCT/US2015/025391.
International Search Report and Written Opinion dated Jul. 2, 2015 which issued in International Patent Application No. PCT/US2015/025396.
Kamen, D.L., et al., "Vitamin D and molecular actions on the immune system: modulation of innate and autoimmunity", J. Mol. Med., vol. 88, pp. 441-450, 2010.
Koch, G., "Effect of 250 and 1000 ppm fluoride dentifrice on caries; a three-year clinical study", Swed Dent J, vol. 6, pp. 233-238, 1982.
Lei, et al., "In Vitro Degradation of Novel Bioactive Polycaprolactone-20% Tricalcium Phosphate Composite Scaffolds for Bone Engineering", Materials and Science and Engineering, vol. 27, Issue 2, Mar. 2007.
Litkowski, et al., "CE4, Intraoral Evaluation of Mineralization of Cosmetic Defects by a Toothpaste Containing Calcium, Fluoride, and Sodium Bicarbonate", Compendium, vol. 25, No. 9, Sep. 2004.
Littarru, G.P., et al., "Deficiency of coenzyme Q10 in gingival tissue from patients wit periodontal disease", Proc. Natl. Acad. Science USA, vol. 68, No. 10, pp. 2332-2335, Oct. 1971.
Lowenstein, et al., "Vaterite: A Mineralization Product of the Hard Tissues of a Marine Organism (Ascidiacea)", Science, vol. 188, pp. 363-365, 1972.
Margolis, H.C., et al., "Physicochemical perspectives on the cariostatic mechanisms of systemic and topical fluorides", J Dent Res, vol. 69 (Special Issue), pp. 606-613, 1990.
Marinho, V.C., et al., "Fluoride varnishes for preventing dental caries in children and adolescents (review)", Cochrane Database Syst Rev, vol. 3, CD002279, 2002.
McCree, J.T., et al., "Therapy with coenzyme Q10 for patients with periodontal disease. Effect of Coenzyme Q10 on Subgingival Microorganisms", Journal of Dental Health, vol. 43, No. 5, pp. 659-666, 1993.
McMahon, L., et al., "Vitamin D-Mediated Induction of Innate Immunity in Gingival Epithelial Cells", Infection and Immunity, vol. 79, pp. 2250-2256, 2011.
Miley, D.D., et al., "Cross-sectional study of vitamin D and calcium supplementation effects on chronic periodontitis", J. Periodontol., vol. 80, No. 9, pp. 1433-1439, Sep. 2009.
Mitropoulos, C.M., et al., "Relative efficacy of dentifrices containing 250 or 1000 ppm F—in preventing dental caries—report of a 32-month clinical trial", Community Dent Health, vol. 1, pp. 193-200, 1984.
Mohammed, N.R., et al., "Effects of Fluoride on in vitro Enamel Demineralization Analyzed by 19F MAS-NMR", Caries Res, vol. 47, pp. 421-428, 2013.
Nakamura, R., et al., "Deficiency of Coenzyme Q in Gingiva Patients with Dental Disease", Internat. J. Vit. Nutr. Res., vol. 43, pp. 85-92, 1973.
Anonymous: "Enamelon Preventive Treatment (gel) Premier Dental Products Company", Jan. 1, 2014, Retrieved from the Internet: URL:https://www.drugs.com/otc/130495/enamelon-preventive-treatment.html.
Supplementary European Search Report issued in EP Application No. EP15776096.8 dated Oct. 24, 2017.
Supplementary European Search Report issued in EP Application No. EP15777496.9 dated Oct. 30, 2017.

* cited by examiner

TOPICAL UBIQUINOL ORAL SUPPLEMENT COMPOSITIONS WITH AMORPHOUS CALCIUM PHOSPHATE

RELATED APPLICATIONS

The subject application is a continuation-in-part of a U.S. patent application entitled "TOPICAL UBIQUINOL SUPPLEMENT SKIN CARE COMPOSITIONS", filed on Oct. 12, 2012, the entire content of which is incorporated by reference.

FIELD OF THE INVENTION

The present invention is directed to stabilized, topical, UBIQUINOL supplement compositions, containing amorphous calcium phosphate fluoride mixtures (ACPF); suitable for adjunctively restoring "local" UBIQUINOL levels in the oral cavity, and remineralizing tooth surfaces of "at-risk" patients indicating: oxidative stress, oral discomfort, dry mouth and demineralized tooth surfaces.

BACKGROUND OF THE INVENTION

UBIQUINOL is the reduced, active antioxidant form of coenzyme Q10 (CoQ10). Produced naturally within healthy bodies, UBIQUINOL is CoQ10 that has been converted (activated by the addition of two electrons). ACPF is a commercial, tooth remineralizing mixture.

"At-risk" patients indicating oxidative stress, oral discomfort and dry mouth, generally indicate demineralization of the hydroxyapatite associated with reduced saliva flow.

UBIQUINOL is considered to be the strongest lipid soluble antioxidant that is biosynthesized, providing an active defense against oxidative insult to lipids, protein and DNA; while maintaining redox balance. See: *THE POWER OF UBIQUINOL*, by Dr. Robert Barry, Ph.D. (2010), Health Point Press, Sherman Oaks, Calif. 91303.

UBIQUINOL supplement is unstable in the presence of oxygen and light, which has limited its use since its commercial introduction in 2008 for oral administration via gelatin capsules. R&D efforts from 2008 to the present by many companies, research organizations, etc., attempting to stabilize UBIQUINOL for topical administration have been unsuccessful.

OBJECTS OF THE INVENTION

An object of the present invention is to stabilize UBIQUINOL supplement in the presence of oxygen and ACPF mixtures.

Another object of the invention is developing a manufacturing process suitable for providing stable UBIQUINOL supplements useful for topical administration, along with ACPF.

Yet another object of the invention is developing a topical UBIQUINOL supplement composition, containing ACPF, suitable for dispensing in gels, pastes, ointments, etc., and via coatings on interproximal devices.

Another object of the invention is to: reduce oxidative stress, reduce oral discomfort, reduce dry mouth, and remineralize tooth surfaces; by topical applications of stable UBIQUINOL compositions, containing ACPF mixtures.

SUMMARY OF THE INVENTION

The present invention is directed to stable, topical, UBIQUINOL supplement compositions containing ACPF mixtures, useful for reducing oxidative stress, relieving oral discomfort and dry mouth and remineralizing tooth surfaces.

Stable UBIQUINOL supplement in compositions of the present invention are represented by the following structural formula:

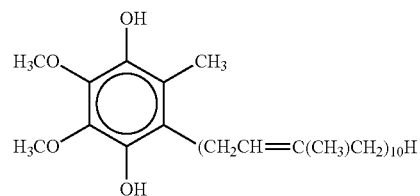

Stable UBIQUINOL supplements for the purposes of this invention include a stabilizing composition comprising: ascorbyl palmitate and propylene glycol.

The UBIQUINOL supplement composition, including a stabilizing composition, is contained in an aqueous-free emulsion along with spilanthes extract and trans-oral mucosal, absorption facilitators.

The present invention is directed to a stable, topical, UBIQUINOL, oral supplement composition useful in: reducing oxidative stress, relieving oral discomfort, relieving dry mouth and remineralizing tooth surfaces; comprising:

a saliva soluble, aqueous-free, emulsion carrier;
an effective level of UBIQUINOL supplement;
a stabilizing composition for UBIQUINOL supplement;
spilanthes extract;
a trans-oral mucosal, absorption facilitator, and
an ACPF mixture, wherein:
  upon application to the oral mucosa, said composition forms a saliva soluble, mucoadhesive gel, substantive to said oral mucosa;
  upon continuous exposure of said saliva soluble, mucoadhesive gel to saliva flow, said mucoadhesive gel gradually dissolves effecting controlled release of said: UBIQUINOL supplement composition, accompanied by a stabilizing composition; trans-oral mucosal, absorption facilitator; spilanthes extract; and the ACPF mixture onto said oral mucosa; and
  upon contacting oral mucosa, said: UBIQUINOL supplement composition; trans-oral mucosal, absorption facilitator; and spilanthes extract passively diffuse through said oral mucosa; while the ACPF mixture remineralizes tooth surfaces:
    (a) reducing oxidative stress;
    (b) restoring and maintaining adequate levels of UBIQUINOL;
    (c) relieving oral discomfort;
    (d) relieving dry mouth; and
    (e) remineralizing tooth surfaces.

Specifically, UBIQUINOL supplement compositions of the invention containing ACPF mixtures, after topical administration to the oral mucosa in aqueous-free, emulsion compositions; form mucoadhesive gels substantive to the oral mucosa. These gels gradually dissolve in the presence of continuing saliva flow, releasing said: UBIQUINOL, with its stabilizing composition, trans-oral mucosal, absorption facilitators and spilanthes extract which, combined, effect passive diffusion of UBIQUINOL supplement and spilanthes extract through the oral mucosa; while simultaneously remineralizing tooth surfaces with the ACPF mixture that is also released from the mucoadhesive gel.

The Role of Topical Ubiquinol Supplement Compositions of the Invention in: Reducing Oxidative Stress, Relieving Oral Discomfort and Relieving Dry Mouth CoQ10 is a fat soluble, essential, quinone molecule, found in every cell, tissue and organ in the body. CoQ10 partners with other enzymes in the body and plays a vital role in cellular and bodily health, including: energy production and free radical production. CoQ10 production in the body decreases with aging. CoQ10 has been shown to have antioxidant potential and to promote ATP production in the mitochondria inner membrane.

Oxidized (ubiquinone) and reduced (ubiquinol) forms have been identified for CoQ10. Ubiquinone is converted by NADPH-dependent CoQ10 reduction, which uses NADPH as an electron donor, into UBIQUINOL. UBIQUINOL is known to exist as the active form of the coenzyme in the body. In a study in which ubiquinone was orally administered to rats, most CoQ10 molecules detected from the lymph were in the form of UBIQUINOL, suggesting that the coenzyme is reduced immediately after being absorbed from the intestinal tract. UBIQUINOL molecules circulating in the body are incorporated into lipoproteins in the liver and are distributed to tissues all over the body via the blood stream.

These molecules appear to be converted to oxidized molecules in the blood when exposed to oxidative stress caused by various factors. However, since the ubiquinone molecules are re-reduced in the liver, over 90% of all CoQ10 molecules present in the blood of a healthy person are in the form of UBIQUINOL, suggesting that the molecules are in a strong reduction condition.

It is well established that CoQ10 (ubiquinone) is not well absorbed into the body, as has been published in many peer-reviewed, scientific journals. Since the reduced CoQ10 (ubiquinol) form has two additional hydrogens, it results in the conversion of two ketone groups into hydroxyl groups on the action portion of the molecule. This causes an increase in the polarity of the CoQ10 molecule and may be a significant factor behind the observed enhanced bioavailability of UBIQUINOL. Orally, UBIQUINOL exhibits greater bioavailability than ubiquinone: 150 mg per day of UBIQUINOL in a softgel resulted in peak blood values of 3.84 mcg/ml within 28 days. Reduced CoQ10 is absorbed faster and in a larger amount than oxidized CoQ10. See U.S. Pat. No. 6,184,255 assigned to KANEKA CORP.

Oxidative stress is detectable as changes in plasma CoQ10 concentrations and composition and plays an important role in oral inflammations experienced by "at-risk" patients. For example, deficiencies of Coenzyme Q10 (CoQ10), both oxidized (ubiquinone) and reduced (ubiquinol), have been implicated in: gums, gingiva and mucosa associated with gingivitis and periodontitis.

"Local" oxidative stress is associated with oral inflammatory conditions experienced by "at-risk" patients, including mucositis, stomatitis, thrush, etc.; and is the target of the topical oral supplement compositions of the invention.

UBIQUINOL is the first lipid soluble antioxidant available for antioxidant defenses in the mouth associated with oxidative stress. UBIQUINOL supplements applied topically to the oral mucosa, via aqueous-free emulsion compositions of the invention, would be the first lipid soluble, antioxidant response to oxidative stress in the oral cavity. In this regard, the plasma redox status of UBIQUINOL in the "local" systemic circulation of the oral cavity provides a measure of "local" systemic oxidative stress.

Adjunctive UBIQUINOL mediated effects on "local" oral inflammatory markers, with the topical supplement compositions of the invention, are expected to indicate reductions in the secretion of several pro-inflammatory cytokines. Damage to nuclear or mitochondrial DNA, indicated by mitochondrial dysfunction caused by biofilm oxidative stress is proposed as a common link among various oral inflammatory conditions.

Gingivitis and periodontitis are inflammatory disorders caused by bacteria living in biofilm. It is known that oxidative stress in the bloodstream and gingiva is increased by oral inflammatory disorders, including: gingivitis and periodontitis. The net effect of this oxidative stress . . . UBIQUINOL deficiencies, which are to be relieved with the compositions of the invention. See:

Littaru, et. al. "Deficiency of coenzyme Q10 in gingival tissue from patients with periodontal disease." (1971) *Proc. Nat. Acad. Science USA* 68:2332-2335.

Nakamura, et. al. "Deficiency of coenzyme Q10 in gingiva of patients with periodontal disease." (1973) *Int. J. Vit. Nut. Res.* 43:84-92.

Therapy of gum disease with UBIQUINOL and coenzyme Q10 (CoQ10) is reported by:

Folkers K (1992) "A critique of 25 years of research which culminated in the successful therapy of periodontal disease with coenzyme Q10." *J. Dent. Health* 42:258-263.

McCree, et. al. (1993) "Therapy with coenzyme Q10 for patients with periodontal disease. Effect of coenzyme Q10 on subgingival microorganisms." *J. Dent. Health* 43:659-666.

Hanioka, et. al. "Effect of Topical Application of Coenzyme Q10 on Adult Periodontitis." (1994 *Molec. Aspects of Med.* Vo. 85 (Supplement) pp. S241-S248.

KANEKA Corp./Nihon University collaborative research on "Effect of the reduced form of coenzyme Q10 (ubiquinol) on oral environment for periodontal disease" presented by K. Sugawara and N. Sugano to: "The $63^{rd}$ Meeting of the Vitamin Society in Japan" held Jun. 4 and 5, 2011 in Hiroshima.

It is well established that oral inflammations, including gingivitis an periodontitis, are accompanied by a deficiency of coenzyme Q10 (both oxidized and reduced versions).

Hanioka, et. al. (1994) topically applied CoQ10 once weekly via syringe to periodontal sites, for six weeks. The authors reported:

"Tremendous improvement was found in bleeding on probing at CoQ10 treated sites after topical application was provided in combination with mechanical debridement."

"Sites bled at day 0 showed no bleeding at six weeks. The effect of treatment was statistically significant only at experimental sites after mechanical subgingival debridement."

"When topical application was provided as a sole treatment, periodontal probing depth, clinical attachment level and gingival crevicular fluid flow showed improvement only at CoQ10 treated sites."

"Thus topical application of CoQ10 might enhance resistance of periodontal tissue to periodontopathic microorganisms."

"improves adult periodontitis not only as a sole treatment but also in combination with traditional nonsurgical periodontal therapy."

However, the amount of CoQ10 absorbed in gingival tissue was not determined in this pilot study.

A June 2011, KANEKA/Nihon University presentation reports that oral administration of UBIQUINOL @ 150 mg capsule/day for two months "is effective in improving oral environment for periodontal disease."

Folkers K. (1992) states:
"CoQ10 is, therefore, recommended for both prophylactic and therapeutic treatment of periodontal disease."
"The indispensability of the intrinsic CoQ10 in boenergetics was emphasized as the basis for the extraordinary healing and the dental benefits resulting from the administration of CoQ10 to periodontal patients."
"It was concluded that CoQ10 can improve bioenergetics and can be prophylactically and adjunctively used for extraordinary healing during routine periodontal therapy."
"It was concluded that this CoQ10 therapy to reduce periodontal disease and particularly microorganisms is preferable to ordinary treatment with antibacterial agents because CoQ10 therapy improves the immune mechanisms to control disease."

From 1994 to date, extensive, published research by Kaneka Corp. on CoQ10 has established:
(a) an increased absorption rate into the bloodstream for reduced coenzyme Q10 (ubiquinol) compared to oxidized CoQ10 (ubiquinone);
(b) there are stability issues affecting UBIQUINOL availability when it is exposed to air and/or light;
(c) procedures have been developed for accurately monitoring plasma levels of ubiquinone and UBIQUINOL; and
(d) a shift in the proportions of subgingival microorganisms of periodontitis patients is attributed to UBIQUINOL adjunctive therapy. Note: This is a key finding for proposed relief of oxidative stress based on administering adjunctive UBIQUINOL aqueous-free emulsion compositions onto the oral mucosa, as described and claimed in the present invention.

Additional relevant references include:
Nylander M. and Nordlund M. (1991). Clinical effects on periodontal status after given oral supplement of ubiquinone. *Swed. J. Biol. Med.* 1, 6-11.
Wilkinson E. G., Arnold R. M., Folkers K., Hansen I. and Kishi H. (1975). Bioenergetics in clinical medicine. II. Adjunctive treatment with coenzyme Q10 in periodontal therapy. *Res. Com. Chem. Path. Pharm.* 12, 111-124.
Wilkinson E. G., Arnold R. M. and Folkers K. (1976). Bioenergetics in clinical medicine. VI. Adjunctive treatment of periodontal disease with coenzyme Q10. *Res. Com. Chem. Path. Pharm.* 13, 715-719.
Hanioka T., Tanaka M., Ojima M., Shizukulski S, and Folkers K. (1994). Effect of topical application of coenzyme Q10 on adult periodontitis. *Molec. Aspects Med.* Vol. 15 (Supplement) S241-S248.
Kishi T., et. al. (1993). *Journal of Dental Health.* 43:667-672.
Shimura Y., et. al. (1981). *Rinsho-to-Kenkyu,* 58, 1349-1352.
U.S. Pat. Nos. 7,897,169; 7,303,921; and 6,184,255.

Inflammation in General and Adjunctive UBIQUINOL Supplements

The present invention is directed to relieving inflammation in the oral cavity that is usually accompanied by "oxidative stress" and reduced UBIQUINOL levels. Adjunctive UBIQUINOL supplement, topically applied by the compositions of the invention to the "local" oral mucosa, reduces oxidative stress, relieves oral discomfort and dry mouth; while also effecting an anti-inflammatory effect as evidenced by reduced circulating markers of inflammation. See: X. Wang, et. al. *Am. J. Clinical. Nutr.* 2004, September; 80(3):649-655:
"Co supplementation with Vitamin E and coenzyme Q10 reduces circulating markers of inflammation in baboons." Vitamin E may be added to the compositions of the present invention.
"Inflammation and oxidative stress are processes that mark early metabolic abnormalities in vascular diseases.
Dietary supplementation with Vitamin E reduces baseline inflammatory status indicated by the CRP concentrations in healthy baboons. Cosupplementation with CoQ10 significantly enhances this anti-inflammatory effect of Vitamin E."

Subsequent "inflammation" studies carried out with ubiquinol by C. Schmelzer, et. al. *J. Clin. Biochem. Nutr.* 44:62-66, January 2009, indicated:
"In vitro effects of the reduced form of coenzyme Q10 on secretion levels of TNF-α and chemokines in response to LPS in the human monocytic celline THP-1"
"In conclusion, our results indicate anti-inflammatory effects of the reduced form of CoQ10 on various inflammatory cytokines and chemokines in vitro."
"Ubiquinol, the reduced form of coenzyme Q10 serves as a potent antioxidant of lipid membranes."

Topical administration of aqueous-free emulsion compositions of the invention form mucoadhesive gels in the presence of saliva, continuously release stable UBIQUINOL supplement onto the oral mucosa, until the gel is dissolved by saliva. This controlled dosage is designed to maximize the therapeutic potential of UBIQUINOL by adjunctively restoring "local" UBIQUINOL deficiencies within circulating lipoproteins at systemic "uptake" rates. Multiple, topical doses of oral gels with aqueous-free emulsion/UBIQUINOL compositions of the invention, throughout the day; provide an ongoing adjunctive response to "local" UBIQUINOL deficiencies caused by oxidative stress. These multiple, topical doses are projected to be responsive to systemic UBIQUINOL uptake. Such a controlled, adjunctive, dosing response to local UBIQUINOL deficiencies caused by oxidative stress is not available from orally administered UBIQUINOL supplement using one or more capsules of UBIQUINOL daily.

Stable UBIQUINOL supplement's low water solubility (less than 0.1 mg/ml) and high molecular weight of 865, results in:
(1) slow absorption of UBIQUINOL supplement from the gastrointestinal tract, i.e. approximately 6 hours required to reach peak concentration, with
(2) steady-state concentrations reached within two weeks of treatment.

In contrast, topical, multiple dose administration of stable UBIQUINOL supplement compositions of the invention, from oral gels and once-a-day-flossing with a dental device, relies on ongoing trans-oral mucosal (sublingual) absorption to directly enter "local" systemic circulation (lymph system, bloodstream, gingiva, etc.). This alternative administration of stable UBIQUINOL supplement compositions of the invention avoids the "first-pass drug effect," which is experienced by orally administered drugs, where the drugs undergo metabolism. This "first pass drug effect" reduces the bioavailability of orally administered, stable UBIQUI- NOL supplement before it reaches systemic circulation. A therapeutic UBIQUINOL plasma level objective of >3.5 µg/ml is projected to be sufficient to reduce the secretions of pro-inflammatory cytokines in the oral cavity associated with oxidative stress. The level of systemic oxidative stress in the oral cavity can be established via the plasma redox status of UBIQUINOL.

Proposed advantages of multiple topical administrations of stable, UBIQUINOL supplement compositions of the invention from an oral gel, applied in repetitive doses throughout the day to "local" oral mucosa under oxidative stress; versus a single oral administration of a comparable quantity of stable UBIQUINOL supplement via capsule, include:

- Efficiency of absorption increases as dose level decreases.
- Bioavailability is optimized by avoiding "first-pass drug effect."
- Maximum therapeutic potential of stable UBIQUINOL is achieved at a faster rate over a longer period of time.
- "Local" UBIQUINOL systemic deficiencies are targeted directly vs. targeting UBIQUINOL deficiencies throughout the body.
- Adjustments in topical administration can be made to accommodate varying UBIQUINOL plasma thresholds for different oral tissues.
- Topical administration of stable UBIQUINOL supplement to the oral mucosa targets restoring "local" UBIQUINOL deficiencies via trans-oralmucosa absorption vs. oral administration of stable UBIQUINOL supplement, which undergoes trans-mucocal absorption in the small intestine and targets restoring UBIQUINOL deficiencies throughout the body.
- A single, topical, "local" administration of 10 to 20 mg of stable UBIQUINOL supplement compositions of the invention from an oral gel extends over the life of the saliva soluble aqueous-free emulsions on the oral mucosa, i.e. 30 to 60 minutes. Such controlled release multiple dosages are responsive to stable UBIQUINOL supplement uptake in the systemic circulation and to the ongoing microflora challenge posed by oxidative stress. This is in contrast to the single oral administration of a 100 to 200 mg capsule of stable UBIQUINOL supplement.
- Multiple, topical administrations of stable UBIQUINOL supplement locally, totaling between 50 and 200 mg carried out over an 8 to 12 hour period, is a more effective response to the continuing inflammatory challenge posed by oxidative stress. This extended topical administration is designed to optimize bioavailability while being responsive to local UBIQUINOL deficiencies attributed to continuing oxidative stress.

UBIQUINOL is considered to be the strongest lipid-soluble antioxidant that is biosynthesized, providing an active defense against oxidative insult to lipids, proteins and DNA.

UBIQUINOL supplement is unstable in the presence of oxygen, which has limited its use since its introduction in 2008 to oral capsules. R&D efforts, from 2008 to the present, by many companies attempting to stabilize UBIQUINOL for topical administration have been unsuccessful.

The present invention represents a major R&D and manufacturing breakthrough in the stabilization and dispensing of Kaneka QH™ UBIQUINOL supplement for Topical applications to the oral mucosa, for relief of oral discomfort attributed to dry mouth and oxidative stress. The present invention relies on aqueous-free emulsion technology, which includes mucoadhesive properties, to transport Kaneka QH™ UBIQUINOL supplement to the oral mucosa for diffusion into the "local" circulatory system. Proprietary: formulating, processing and dispensing conditions for this combination: assures that the oxidative properties of Kaneka QH™ UBIQUINOL supplement have not been compromised and that "reduced" Kaneka QH™ UBIQUINOL is delivered topically to the oral mucosa.

Up to the present, restoration of UBIQUINOL deficiencies associated with dry mouth, has been primarily through adjunctive Kaneka QH™ UBIQUINOL supplement capsules administered orally. See references enclosed.

The "intensive care" ORAL GEL supplement compositions of the present invention rely on topical administration of UBIQUINOL/aqueous-free emulsions that form mucoadhesive gels on the mucosa. This proprietary, mucoadhesive gel continually releases:

(1) Spilanthes extract, to enhance saliva flow; and
(2) Kaneka QH™ UBIQUINOL supplement (in the reduced state accompanied by a UBIQUINOL stabilizing composition), along with a trans-oral mucosal absorption facilitator.

The stabilized Kaneka QH™ UBIQUINOL supplement, in combination with its mucosal absorption facilitator, is continuously released from the mucoadhesive gel, followed by diffusion of UBIQUINOL supplement through the mucosa. The stabilized Kaneka QH™ UBIQUINOL supplement, combined with an absorption facilitator, enters the "local": bloodstream, lymph, gingiva and/or salivary glands via "passive diffusion" through the oral mucosa. This topical, adjunctive administration of UBIQUINOL "intensive care" ORAL GEL is projected to help: restore "local" ubiquinol deficiencies, increase saliva flow, restore salivary glands damaged by oxidative stress and provide relief from oral discomfort as discussed in the cited references.

This trans-oral mucosal absorption of Kaneka QH™ UBIQUINOL supplement, in the reduced state, continues until the mucoadhesive gel is dissolved by saliva. The substantivity of the mucoadhesive gel to the oral mucosa can be extended with various resin modifications to the mucoadhesive gel. For optimum results, multiple topical applications of UBIQUINOL "intensive care" ORAL GEL are recommended throughout the day.

Topical UBIQUINOL Supplement Compositions of the Invention Feature

- Stabilized, Kaneka QH™, UBIQUINOL SUPPLEMENT maintained in a proprietary, aqueous-free emulsion in a reduced state until the emulsion is exposed to saliva forming a mucoadhesive gel that is eventually solubilized by saliva and the UBIQUINOL supplement passively diffuses into the oral mucosa.
- Topical, direct and rapid, adjunctive supplementation of "local", depleted, UBIQUINOL levels in the oral mucosa resulting in the restoration of a healthy redox balance.
- Stabilized, Kaneka QH™, UBIQUINOL supplement, combined with an oral mucosal absorption facilitator, ensures rapid, optimal absorption and assimilation by the "local" oral mucosa.
- Neutralizing free radicals in the local oral mucosa, thereby preventing cellular damage of the mucosa that would otherwise contribute to or exacerbate diseases of "intensive care" patients.

Providing the "local" oral mucosa, of "intensive care" patients, an ongoing active defense against oxidative insult to: lipids, proteins and DNA.

Helping relieve oral discomfort for those "intensive care" patients suffering from a range of oral conditions related to oxidative stress, including:
  dry mouth: xerostomia, Sjogren's disease, lupus, etc.;
  inflammation: gingivitis, periodontitis, periodontitis implantitis, mucositis, stomatitis, etc.;
  oral care specialist treatments by: periodontists, orthodontists, endodontists, oral surgeons, etc.;
  medical procedures for: cancer, diabetes, COPD, cardiovascular conditions, etc.; and/or
  various systemic conditions of "intensive care" patients, resulting in "free-radical-based" oxidative stress.

Topical, Adjunctive Supplementation with the Stable, UBIQUINOL Supplement Compositions of the Invention for "Intensive Care" Dry Mouth Patients Protect "local" oral mucosa cells with an extremely powerful antioxidant that features a strong protective defense against oxidative stress and dry mouth.

Not only effect: rapid, direct diffusion of UBIQUINOL SUPPLEMENT into the "local" oral mucosa; but also avoid the "first-pass effect" associated with orally administered Kaneka QH™ UBIQUINOL SUPPLEMENT capsules . . . while providing rapid, lasting, "local" relief from oral discomfort associated with oxidative stress and dry mouth.

Is considered a vital topical supplement for "intensive care" dry mouth patients seeking to maintain a healthy lifestyle.

All of the references cited herein, are hereby, in their entirety, incorporated by reference into the present invention.

The Role of ACPF Mixtures in Remineralizing Tooth Surfaces

The remineralizing properties of amorphous calcium phosphate fluoride mixtures are described: by Ming Tung in U.S. Pat. Nos. 5,037,639; 5,268,167; 5,427,768; 5,437,857; 5,460,803; 5,562,895; by Tung in the American Dental Association Foundation publication, "ACP Technology,"; by Schemahorn, et. al., in *The Journal of Clinical Dentistry* Vol. XXII: No 2. 51-54, 2011; and by the 19 references cited by Schemahorn, et. al.

Amorphous calcium phosphate is described by Wikipedia as follows:

"Amorphous calcium phosphate (ACP) is a substance used as a dental treatment. Calcium and phosphate are natural building blocks of teeth, and when present in insufficient amounts, there can be sensitivity after procedures such as dental bleaching or professional dental cleansing. Amorphous calcium phosphate will help in restoring the necessary mineral balance in the mouth in an easy and efficient way.

"ACP technology using a two-phase delivery system that prevents the calcium and phosphate from reacting was developed by Ming S. Tung at the American Dental Research Association's Paffenbarger Research Center. It was first used in a toothpaste called Enamelon in 1999, but it failed commercially. It is now found in Arm & Hammer's Enamel Care Toothpaste (introduced in 2004) as well as their Age Defying Toothpaste, Discus Dental's Nite White bleaching gel, Discus Dental's Relief ACP sensitivity relief product, and Premier Dental's Enamel Pro polishing paste. It is also used in the Aegis product line, such as Aegis® Pit and Fissure Sealant with ACP, produced by the Harry J. Bosworth Company for use by dental professionals. Other Aegis Products include: Aegis® Orthodontic Adhesive with ACP, Aegis® Liner with ACP, Aegis® V with ACP and Aegis® Crown and Bridge with ACP."

According to Ming Tung, after the ACPF salts in the aqueous-free emulsions are dissolved in saliva, they precipitate and hydrolyze to tooth mineral as follows: In an acidic environment, the following reactions occur rapidly; leading to remineralization of interproximal tooth surfaces that have been physically cleaned:

The $Ca^{2+}$ and $X^{2+}$ $(HPO_4)^{2-}+F^-$ ions precipitate as $CaF_2Ca_9X(PO_4)_6F_2(ACXPF)$.

Subsequent hydrolysis of this precipitate releases fluoridated tooth mineral:

$$Ca_{10}(PO_4)_6F_2+F^-+(H_{1.5}PO_4)^{1.5}+OH+X^{24}$$

Aqueous-free emulsions of the invention, containing:
  calcium gluconate,
  calcium lactate, gluconate,
  disodium hydrogen phosphate,
  sodium fluoride, and
  citric acid;
hold the various salts in suspension without the salts reacting. When this emulsion is exposed to saliva, it forms a mucoadhesive gel that is substantive to tooth surfaces.

Eventually, this mucoadhesive gel is dissolved by saliva, releasing the ACPF components onto the hydroxyapatite. The ACPF components penetrate the hydroxyapatite and form amorphous calcium phosphate fluoride precipitates in the hydroxyapatite.

A remineralizing, functional, aqueous-free emulsion of the invention contains stable cations and stable anions, suitable for reacting to remineralize dental enamel; wherein:
  (1) said aqueous-free emulsion inhibits premature reaction of the cations with the anions;
  (2) the cations and anions are introduced onto tooth surfaces via saliva soluble, mucoadhesive gels that are substantive to: hydroxyapatite, dentin, biofilm, pellicle and soft tissue;
  (3) the cations and anions are released onto the hydroxyapatite as the saliva soluble, mucoadhesive gels undergo dissolution at rates generally controlled by saliva flow;
  (4) local saliva flow can be further controlled by spilanthes extract introduced onto tooth surfaces from said aqueous-free emulsion;
  (5) local pH environment for said dissolving gels is controlled, in part, by ascorbyl palmitate present in said aqueous-free emulsion, where said ascorbyl palmitate also assists in substantivity of the various cations and anions released onto tooth surfaces by dissolution of said mucoadhesive gels;
  (6) said saliva soluble gel controls the rate of release of cations onto tooth surfaces, thereby controlling diffusion of said cations into demineralized subsurfaces and/or into dentinal tubules;
  (7) said saliva soluble gel controls rate of release of anions onto tooth surfaces, thereby controlling diffusion of said anions into demineralized subsurfaces and/or into exposed dentinal tubules;

(8) said solubilized cations and anions, after diffusing into demineralized subsurfaces and/or into exposed dentinal tubules: react, precipitate in an amorphous state and remineralize;
(9) said aqueous-free emulsion comprises polydimethylsiloxane, at various molecular weights emulsified in nonionic surfactants comprised of copolymers comprised of polyoxypropylene and polyoxyethylene; and
(10) said remineralizing, functional, aqueous-free emulsions can be dispensed via: dental tape, toothpaste, prophy paste, fluoride varnishes, fluoride gels, dry mouth gels and combinations thereof.

DETAILED DESCRIPTION OF PRESENTLY PREFERRED EMBODIMENTS

In a preferred embodiment of the invention, UBIQUINOL supplement compositions, containing ACPF mixtures, are included in a topical, oral supplement of the invention; where the UBIQUINOL supplement composition: reduces oxidative stress by increasing "local" UBIQUINOL levels, relieving oral discomfort and dry mouth, while remineralizing tooth surfaces.

The present invention includes methods:
for reducing oxidative stress, relieving oral discomfort and dry mouth, and remineralizing tooth surfaces; comprising topically administering UBIQUINOL supplement compositions of the invention onto the oral mucosa, comprising:
a saliva soluble, aqueous-free emulsion carrier for UBIQUINOL supplement;
effective levels of UBIQUINOL supplement;
a stabilizing composition for UBIQUINOL comprising acorbyl palmitate, propylene glycol and carboxymetholcelluose in a weight-ratio to UBIQUINOL from between about 1.5 and 2.5;
spilanthes extract;
trans-oral mucosal, absorption facilitators; and
an ACPF mixture, wherein:
  upon application to the oral mucosa, said composition forms a saliva soluble, mucoadhesive gel, substantive to said oral mucosa;
  upon continuous exposure of said saliva soluble, mucoadhesive gel to saliva flow, said mucoadhesive gel gradually dissolves effecting controlled release of said: UBIQUINOL supplement, including the stabilizing compositions; trans-oral mucosal, absorption facilitators; spilanthes extract; and ACPF mixtures onto said oral mucosa;
wherein application means for said topical UBIQUINOL oral supplement composition are selected from the group consisting of interproximal devices coated with said composition, oral gels, oral ointments, oral pastes, oral varnishes, oral liquids and combinations thereof; and
wherein the UBIQUINOL supplement compositions of the invention are topically administered repetitively throughout the day with UBIQUINOL supplement gels, in combination with daily, topical administration with a dental device coated with UBIQUINOL supplement compositions of the invention.

UBIQUINOL compositions, suitable for topical administration to the oral mucosa, include: an aqueous-free emulsion carrier for the supplement mixture that also contains: a stabilizing composition for the UBIQUINOL, trans-oral mucosal absorption facilitators, spilanthes extract and an ACPF mixture; wherein: said aqueous-free emulsion, upon exposure to saliva, forms a mucoadhesive gel substantive to the oral mucosa. Upon saliva dissolution of this mucoadhesive gel, UBIQUINOL with stabilizing composition/trans-oral mucosal, absorption facilitator/spilanthes extract gradually releases from the mucoadhesive gel to passively diffuse through the oral mucosa, thereby increasing "local" levels of UBIQUINOL; while the released ACPF mixture remineralizes tooth surfaces.

Topical administration of the UBIQUINOL supplement composition of the invention to the oral mucosa is preferably carried out with oral gels or dental devices coated with UBIQUINOL compositions of the invention. Particularly preferred, topical administration of the supplement to the oral mucosa is effected by a combination of several administrations of the supplement composition of the invention in a topical gel throughout the day, combined with once or twice daily flossing with a dental device composition coated with the UBIQUINOL supplement compositions of the invention.

For purposes of the present invention, saliva soluble, aqueous-free emulsions include those emulsions that are comprised of polydimethylsiloxane in a nonionic surfactant, as described in the following U.S. Pat. Nos. 5,032,387; 5,098,711; 5,538,667 and 5,651,959; all of which are hereby incorporated by reference.

Preferred nonionic surfactants of the invention capable of forming a mucoadhesive gel in the presence of saliva. These are selected from the group consisting of: poloxamer 237, poloxamer 338, poloxamer 407 and combinations thereof.

For the purposes of the present invention, trans-oral mucosal, absorption facilitators are selected from the group consisting of: dexpanthenol, d-Limonene, poloxamer, PEG, benzyl alcohol, carbopol, chitosan, N-trimethylchitosan, menthol and combinations thereof.

Preferred aqueous-free, saliva soluble emulsions for use as carriers of for UBIQUINOL supplement in the compositions of the present invention include emulsions of polydimethylsiloxane (PDMS) at viscosities ranging from between about 1500 cs and about 2.5 million cs. Particularly preferred, aqueous-free emulsions include as the discontinuous phase PDMS at viscosities between 10,500 cs and 2.5 million cs with those nonionic surfactants described in detail in U.S. Pat. No. 5,651,959, as the continuous phase.

Preferred polydimethylsiloxanes are selected from the group consisting of polydimethylsiloxane: at 1500 cs, at 12,500 cs, at 100,000 cs, at 250,000 cs, at 500,000 cs, at 750,000 cs, at 1.5 million cs, at 2.2 million cs, at 2.5 million cs and combinations thereof.

Preferred application means for the UBIQUINOL oral supplement compositions of the present invention include: oral gels, oral ointments, oral pastes, oral varnishes, oral liquids and various interproximal devices coated with said UBIQUINOL oral supplement compositions.

Preferred oral gels for purposes of the present invention include those gels disclosed in U.S. Pat. Nos. 5,009,881; 5,032,387; 5,057,306; 5,057,307; 5,057,309; 5,538,667 and 5,651,959; all of which are included herein by reference.

Preferred coated, interproximal devices, suitable for releasing UBIQUINOL oral supplement compositions interproximally, include those interproximal devices described in the following U.S. Pat. Nos. 4,911,927; 4,942,034; 5,098,711; 5,165,913; 5,665,374; 5,711,935; 6,545,077; 6,575,176; 7,017,591; 7,025,986 and 7,152,611; all of which are hereby included by reference.

The use of dental devices is an extremely important adjunct to proper dental hygiene. Dental devices have long been used effectively to clean the spaces between the teeth and under the gingival margin. When used properly, dental devices have been found to be effective in inhibiting tooth decay and gum disease. They are recommended by dentists for daily dental hygiene.

To increase the effectiveness of the dental devices, some devices have included certain medicinal ingredients or dentifrice components to help protect the tooth enamel from acid attack. Bactericides have also been used in connection with dental floss to inhibit periodontal disease.

Other active components which may be incorporated within the interproximal device include hydrogen peroxide or other peroxide-producing components such as PVP $H_2O_2$ or Carbamide $H_2O_2$ Fluoride, tooth acidulating agents such as buffered or acidulated phosphofluoride, sodium monofluorophosphate, plaque control agents, tartar control agents, antibiotics to treat pyorrhea and gingivitis, teeth whitening and bleaching agents, pH buffering agents, antifungal agents, remineralizing agents, hemostatic agents, immunological agents and nonionic and cationic antibacterials such as benzothonium chloride, acetyl trimethyl ammonium bromide, sanguinaria, triclosan (nonionic), tetracycline, cetyl pyridinium chloride and benzythonium chloride.

Additional active components that can be included in the dental devices of the present invention include Vitamin A, surfactants and pharmacological agents such as anti-cancer agents, stimulants, bone growth agents, antigens, hormones, steroids, anti-inflammatory agents and analgesic agents.

In other embodiments, the dental device comprises a coagulant to inhibit any bleeding which may be produced by flossing. Preferably, the coagulant is mixed in the wax coating so as to directly contact the gum tissue. The coagulants may include vitamin K, calcium ions in the form of water-soluble calcium salts and blood factors that initiate the coagulation cascade. Alternatively, the coagulants may be solubilized in non-toxic solvents, such as ethanol, polyethylene terepthalate or diethyl ether.

Flavorants may be added to the dental devices of the present invention by techniques known in the art, such as adding the flavorant directly to the device after extrusion or by applying a flavored coating to the surface of the device, or by transferring volatile flavors to the device from a flavor reservoir. Known flavorants such as mint, cinnamon and bubble gum, which are commercially available through various suppliers including IFF Corporation, Dayton, N.J.; are suitable for use in the dental devices of the present invention. Other flavorants may also be added by the compression coating process described in the references cited.

Colorants may be added to the dental devices of the present invention to color the dental device in order to provide a visual stimulus to the consumer. Colorant can be added to the nylon or other pellets used to form the strand before extrusion begins. Any one of commercially available, FDA approved colorants for use with nylon resins may be used. Colors may correspond to the flavor of the dental device, e.g., red for cinnamon or green for mint. Further, multiple colors may be extruded simultaneously so that, for example, one side of the filament is red and other green. The device may further incorporate colorant agents or fluorescent dye to identify residual plaque deposits, such as, for example, FD&C Red 3 and FD&C Red 4.

EXAMPLES 1-13

The present invention is further described by additional enclosed samples of topical gels and dental tapes used to apply the UBIQUINOL supplement compositions of the invention to the oral mucosa and to interproximal surfaces, respectively.

Example 1—UBIQUINOL/ACPF Oral Gel

A Hobart N-50 mixer fitted with a 1 gallon stainless steel bowl and a nitrogen blanket were used to mix the following: PEG 400, 272 gm; aqueous-free emulsion [poloxamer 407/polydimethylsiloxane (90:10)], 64 gm; poloxamer 407, 183.2 gm; pluracol L-1220, 183.2 gm; Carbopol 974P, 16 gm; glycerin, 580.72 gm; xylitol powder, 48 gm; acesulfame K, 4.8 gm; titanium dioxide, 16 gm; zeodent 113, 80 gm; sipernat 22S, 120 gm; perlastin L, 8 gm; sucralose, 2.4 gm; flavor, 21.6 gm were stirred for 5 minutes at room temperature. The contents of the bowl were heated to 80 degrees Centigrade. Ubiquinol, 12 gm and ascorbyl palmitate, 12 gm, were added to the bowl under a nitrogen blanket with carboxymethyl cellulose, 30 gm while mixing Calcium gluconate, 128 gm; calcium lactate gluconate, 44.8 gm; and disodium hydrogenphosphate, 25.6 gm, with stirring under nitrogen. After stirring for 5 minutes, the contents of the one gallon vessel were dispensed into 40 gm tubes for topical application. Application of 1 gram of gel to the oral mucosa delivers ubiquinol supplement and amorphous calcium phosphate fluoride, remineralizing from a mucoadhesive gel substantive to the oral mucosa.

Example 2—UBIQUINOL/ACPF Prophy Tape

A 2 gallon stainless steel vessel was fitted with an overhead stirrer and place on a hotplate. Aqueous-free emulsion [poloxamer 407/polydimethylsiloxane (12,500 CS) 90:10], 945.63 gm and 1080 gm of poloxamer 407 were placed in the vessel and melted while stirring under a nitrogen blanket. The temperature rose to 90 degrees Centigrade and the following ingredients were added: Pluracare L-1220, 120 gm; stearyl alcohol, 450.8 gm; microwax ML445, 267.6 gm and PEG 8000, 388 gm, were added to the molten aqueous-free emulsion. A homogenizer was placed in the vessel and emulsification resulted from 10 minutes of action. The following ingredients were then added with stirring: Calcium gluconate, 240 gm; Calcium lactate gluconate, 84 gm; disodium hydrogen phosphate, 48 gm; sodium fluoride, 4.4 gm; propyl gallate, 4 gm; sodium saccharin, 96 gm; EDTA, 8 gm; flavor, 104 gm and citric acid, 40 gm. Ubiquinol, 30 gm; ascorbyl palmitate, 30 gm and carboxymethylcellulose, 60 gm, were added with stirring for 5 minutes under a nitrogen atmosphere. The emulsified tape coating batter was then dispensed into the tape coating tank. Compression coating of ultra-high-molecular-weight polyethylene dental tape at 64 mg/yard was completed to give a saliva soluble coated dental tape with ubiquinol supplement and amorphous calcium phosphate fluoride remineralizing from a mucoadhesive gel substantive to tooth and mucosa surfaces.

Example 3

A 30 mL glass vial was fitted with a magnetic stirrer and a nitrogen flush while 5 gm of an aqueous-free emulsion of poloxamer 407/polydimethylsiloxane (2.5 million cs) was melted at 80-90 degrees C. Ascorbyl palmitate, 1 gm, was added with stirring. UBIQUINOL, 1 gm, was then added and finally, 8.37 gm of propylene glycol was added with continuing heating and stirring under nitrogen for 10-15 minutes. The vial was removed from stirring and heating and allowed to come to room temperature. The initial sample of UBIQUINOL had a slight yellow color due to exposure to air as a result to opening of a sealed package of UBIQUINOL. The experimental vial's relative color was compared to initial yellow level at first addition. After setting at room temperature for 24 hours, the color was evaluated. The sample color was medium yellow, indicating very little reduction of the CoQ10 contaminate by the ascorbyl palmitate.

A number of examples were prepared under the same conditions described for Example 3 with 5 gm of the aqueous-free emulsion (80% poloxamer 407 emulsified with polydimethylsiloxane, 2.5 million cs), ascorbyl palmitate at 1 gm and UBIQUINOL at 1 gm, as above:

Examples 3 to 11

| Example # | Composition | Other components added | Color Results |
|---|---|---|---|
| 3 | as executed in Example 3 | none | medium yellow |
| 4 | as executed in Example 3 | 2.39 gm glycerin added | medium yellow |
| 5 | as executed in Example 3 | 0.19 gm of methyl paraben | medium yellow |
| 6 | 5 gm of emulsion, 1 gm ascorbyl palmitate, 1 gm ubiquinol, | 1.85 gm of carboxy-methyl-cellulose 9H4XF | medium yellow |
| 7 | as executed in Example 6 | 8.37 gm propylene glycol | all white |
| 8 | as executed in Example 6 | 1.0 gm carboxy-methyl-cellulose 9H4XF | medium yellow |
| 9 | as executed in Example 7 | 0.5 gm carboxy-methyl-cellulose 9H4XF | medium yellow |
| 10 | as executed in Example 6 | 1.0 gm carboxy-methyl-cellulose 9H4XF | mottled yellow and white |
| 11 | as executed in Example 7 | 0.5 gm carboxy-methyl-cellulose 9H4XF | mottled yellow and white |

These results indicate that the formulation comprising an aqueous-free emulsion, comprising UBIQUINOL, ascorbyl palmitate, propylene glycol and an amount of carboxymethylcellulose in a weight ratio from between about 1.5 and 2.5, imparts stability to UBIQUINOL, allowing topical UBIQUINOL compositions to adjunctively supplement UBIQUINOL levels.

Example 12—UBIQUINOL Supplement Gel with ACPF

A 2 liter stainless steel vessel was fitted with an overhead stirrer, hotplate and an aluminum foil cover with nitrogen flush. The following ingredients were added with stirring and heating to 90 degrees C.: PEG 400, 200 gm; an aqueous-free emulsion [poloxamer 407/polydimethylsiloxane (2.5 million cs)] (90:10) 25 gm; carbopol 974P, 8.5 gm; glycerin, 505.8 gm; xylitol, 50 gm; acesulfame K, 3 gm; titanium dioxide, 10 gm; calcium gluconate, 75 gm; calcium lactate gluconate, 26.2 gm; disodium hydrogen phosphate, 15 gm; perlastin L, 10 gm; sucralose, 1.5 gm; flavor 10 gm; zeodent 113.25 gm; sipernat 22S, 15 gm; Kaneka QH™ UBIQUINOL SUPPLEMENT, 5 gm; ascorbyl palmitate, 5 gm; carboxymethylcellulose, 7.5 gm; and citric acid, 10 gm. Stirring was continued until homogeneous. The UBIQUINOL SUPPLEMENT GEL with ACPF was packaged in tubes under a blanket of nitrogen for topical application to the oral mucosa and tooth surfaces.

Example 13—UBIQUINOL Supplement Prophy Tape® ACPF

A 2 gallon stainless steel vessel was fitted with an overhead stirrer and placed on a hotplate. A homogenizer was fitted and a nitrogen flush was added to the covered, stirred vessel. An aqueous-free emulsion [poloxamer 407/polydimethylsiloxane (2.5 million cs)] (90:10) 915.28 gm, was placed in the vessel and melted while stirring. The temperature rose to 90 degrees C. The following ingredients were added to the molten aqueous-free emulsion: Poloxamer 407, 1160 gm; pluracare L-1220, 120 gm; stearyl alcohol, 418.8 gm; microwax ML445, 267.6 gm; and PEG 8000, 356 gm. A homogenizer was placed in the vessel and emulsification via homogenizing resulted from 15 minutes of action. The following ingredients were then added with stirring: calcium gluconate, 300 gm; calcium lactate gluconate, 104.8 gm; disodium hydrogen phosphate, 60 gm; sodium fluoride, 5.52 gm; propyl gallate, 4 gm, sodium saccharin, 96 gm, EDTA, 8 gm; and citric acid, 40 gm. Finally, Kaneka QH™ UBIQUINOL SUPPLEMENT, 20 gm; ascorbyl palmitate, 20 gm; and carboxymethylcellulose, 30 gm, were added to the emulsified composition. After further stirring, the emulsified tape coating batter was then transferred into the tape coating tank. Compression coating of ultra-high-molecular-weight polyethylene dental tape was completed at between 50 and 60 mg/yd. The compression coated tape was overcoated with bioglass SOFT ABRASIVE® at between 6 and 11 mg/yd. The overcoated tape was cut into 20 inch pieces, wrapped in paper and folded. The folded tape pieces were placed in flavor-sealed packages with a flavor reservoir containing about 25 drops of volatile flavor. On storage, the tape pieces were flavored with hi-impact flavor, via flavor transfer.

What is claimed is:

1. An aqueous free ubiquinol composition, containing an amorphous calcium phosphate fluoride (ACPF) mixture, useful in topically reducing oxidative stress, relieving oral discomfort and dry mouth, and remineralizing tooth surfaces; comprising:
    a saliva-soluble, aqueous-free, emulsion carrier;
    an effective level of ubiquinol;
    a stabilizing composition for ubiquinol comprising an effective amount of ascorbyl palmitate, propylene glycol, and carboxymethylcellulose, wherein the amount of carboxymethylcellulose is present in a percent ratio to the amount of ubiquinol between about 1.5 and about 2.5, and the weight ratio of the ascorbyl palmitate, propylene glycol, ubiquinol, and carboxymethylcellulose to aqueous-free emulsion, is between 1.5 and 2.5;
    spilanthes extract;
    a trans-oral mucosal absorption facilitator;
    an ACPF mixture comprising calcium gluconate, calcium lactate gluconate, disodium hydrogen phosphate, sodium fluoride, and citric acid,
    and wherein:
    (i) upon application to the oral mucosa, said composition forms in situ in the oral cavity a saliva-soluble, mucoadhesive gel that is substantive to said oral mucosa;
    (ii) said ubiquinol in the composition and resulting gel is stabilized, in that its conversion to ubiquinone is inhibited;

(iii) upon continuous exposure of said saliva-soluble, mucoadhesive gel to saliva flow, said mucoadhesive gel gradually dissolves effecting controlled release of said ubiquinol, stabilizer composition for ubiquinol, trans-oral mucosal absorption facilitator, spilanthes extract and ACPF mixture onto said oral mucosa; and (iv) upon contacting said oral mucosa, said ubiquinol, spilanthes extract and trans-oral mucosal absorption facilitator passively diffuse through said oral mucosa, while said ACPF mixture remineralizes tooth surfaces:
  (a) reducing oxidative stress;
  (b) restoring and maintaining adequate local levels of ubiquinol;
  (c) relieving oral discomfort;
  (d) relieving dry mouth; and
  (e) remineralizing tooth surfaces.

2. The composition according to claim 1, wherein said saliva-soluble, aqueous-free emulsion comprises polydimethylsiloxane emulsified in a nonionic surfactant that is capable of forming a mucoadhesive gel in the presence of saliva.

3. The composition according to claim 1, wherein said ubiquinol is represented by the structural formula:

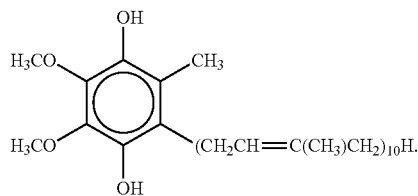

4. The composition according to claim 1, wherein said trans-oral mucosal absorption facilitator is selected from the group consisting of dexpanthenol, d-Limonene, poloxamer, polyethylene glycol (PEG), benzyl alcohol, carbopol, chitosan, N-trimethylchitosan, menthol and combinations thereof.

5. The composition according to claim 1, wherein application means for said ubiquinol composition is selected from the group consisting of interproximal devices coated with said composition, oral gels, oral ointments, oral pastes, oral varnishes, oral liquids and combinations thereof.

6. A composition, according to claim 5, wherein said interproximal device application means is selected from the group consisting of compression coated dental tape, multifilament or monofilament dental floss, coated one-handed dental devices, dental picks, dental stimulators and combinations thereof.

7. The composition according to claim 2, wherein said polydimethylsiloxane is selected from the group consisting of polydimethylsiloxane at 1,500 cs, at 12,500 cs, at 100,000 cs, at 250,000 cs, at 500,000 cs, at 750,000 cs, at 1.5 million cs, at 2.2 million cs, at 2.5 million cs and combinations thereof.

8. The composition according to claim 2, wherein said nonionic surfactant is selected from the group consisting of poloxamer 237, poloxamer 338, poloxamer 407 and combinations thereof.

9. The composition according to claim 1, wherein said ubiquinol adjunctively supplements local ubiquinol levels, thereby reducing oxidative stress.

10. The composition of claim 1 wherein the components are included according to the following ratios to one another: 5 gm of aqueous free emulsion to 1 gm of ascorbyl palmitate to 1 gm of ubiquinol, to 1.85 gm of carboxymethyl-cellulose, and to 8.37 gm of propylene glycol.

11. An aqueous free oxygen-resistant ubiquinol composition containing an ACPF mixture, useful in topically reducing oxidative stress, relieving oral discomfort and dry mouth, and remineralizing tooth surfaces; comprising:
  a saliva-soluble, aqueous-free emulsion of polydimethylsiloxane as the discontinuous phase and a nonionic poloxamer surfactant as the continuous phase emulsion carrier;
  an effective level of ubiquinol;
  a stabilizing composition for ubiquinol comprising an effective amount of ascorbyl palmitate, propylene glycol, and carboxymethylcellulose, wherein the amount of carboxymethylcellulose is present in a percent ratio to the amount of ubiquinol between about 1.5 and about 2.5, and the weight ratio of the ascorbyl palmitate, propylene glycol, ubiquinol, and carboxymethylcellulose to aqueous-free emulsion, is between 1.5 and 2.5,
  an ACPF mixture comprising calcium gluconate, calcium lactate gluconate, disodium hydrogen phosphate, sodium fluoride, and citric acid;
  spilanthes extract of about at least 0.2 percent; and
  a trans-oral mucosal absorption facilitator; wherein said composition is substantially free from ubiquinone, and wherein:
  (i) upon application to the oral mucosa, said composition forms in situ in the oral cavity a saliva-soluble, mucoadhesive gel that is substantive to said oral mucosa;
  (ii) upon continuous exposure of said saliva-soluble, mucoadhesive gel to saliva flow, said mucoadhesive gel gradually dissolves effecting controlled release of said ubiquinol, stabilizer composition for ubiquinol, trans-oral mucosal absorption facilitator, spilanthes extract and ACPF mixture onto said oral mucosa; and
  (iii) upon contacting said oral mucosa, said ubiquinol, spilanthes extract and trans-oral mucosal absorption facilitator passively diffuse through said oral mucosa, resulting in a ubiquinol plasma level of at least about 3.5 µg/ml, while said ACPF mixture remineralizes tooth surfaces:
    (a) reducing oxidative stress;
    (b) restoring and maintaining adequate local levels of ubiquinol;
    (c) relieving oral discomfort;
    (d) relieving dry mouth; and
    (e) remineralizing tooth surfaces.

12. A method for relieving: oxidative stress, oral discomfort and dry mouth, and for reducing demineralization of tooth surfaces; comprising topically, adjunctively administering an aqueous free ubiquinol supplement compositions, containing ACPF mixtures, to the oral mucosa; comprising:
  a saliva soluble, aqueous-free emulsion carrier;
  an effective level of ubiquinol supplement in a stabilizing composition wherein the stabilizing composition comprises an effective amount of ascorbyl palmitate, propylene glycol, and carboxymethylcellulose, wherein the amount of carboxymethylcellulose is present in a percent ratio to the amount of ubiquinol between about 1.5 and about 2.5, and the weight ratio of the ascorbyl palmitate, propylene glycol, ubiquinol, and carboxymethylcellulose to aqueous-free emulsion, is between 1.5 and 2.5;
  spilanthes extract;
  a trans-oral mucosal, absorption facilitator; and an ACPF mixture comprising calcium gluconate, calcium lactate gluconate, disodium hydrogen phosphate, sodium fluoride, and citric acid, wherein said ubiquinol supplement compositions are substantially aqueous free, and wherein:

upon application to the oral mucosa, said composition forms a saliva soluble, mucoadhesive gel, substantive to said oral mucosa;

upon continuous exposure of said saliva soluble, mucoadhesive gel to saliva flow, said mucoadhesive gel gradually dissolves effecting controlled release of said: ubiquinol supplement, stabilizing composition for ubiquinol, trans-oral mucosal, absorption facilitator, spilanthes extract and ACPF mixtures onto said oral mucosa; and upon contacting said oral mucosa, said: ubiquinol supplement, spilanthes extract and trans-oral mucosal, absorption facilitator passively diffuse through said oral mucosa; while the ACPF mixture remineralizes tooth surfaces:
(a) reducing oxidative stress;
(b) restoring and maintaining adequate levels of ubiquinol;
(c) relieving oral discomfort;
(d) relieving dry mouth; and
(e) remineralizing tooth surfaces.

13. A method, according to claim 12, wherein said saliva soluble, aqueous-free emulsion is comprised of polydimethylsiloxane emulsified in a nonionic surfactant that is capable of forming a mucoadhesive gel in the presence of saliva.

14. A method, according to claim 12, wherein said ubiquinol supplement is represented by the structural formula:

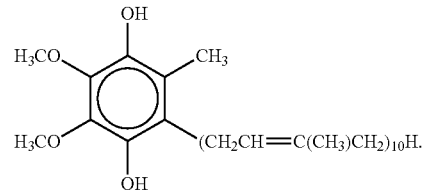

15. A method, according to claim 12, wherein said trans-oral mucosal, absorption facilitators are selected from the group consisting of: dexpanthenol, d-Limonene, poloxamer, PEG, benzyl alcohol, carbopol, chitosan, N-trimethylchitosan, menthol and combinations thereof.

16. A method, according to claim 12, wherein application means for said topical ubiquinol, oral supplement composition is selected from the group consisting of interproximal devices coated with said composition, oral gels, oral ointments, oral pastes, oral varnishes, oral sealants, oral rinses, oral liquids and combinations thereof.

17. A method for relieving: oxidative stress, oral discomfort, dry mouth and demineralization of tooth surfaces; comprising topically administering said ubiquinol supplement composition, according to claim 12, wherein said composition is applied as a gel repetitively throughout the day; in combination with daily topical administration with a dental device coated with said ubiquinol supplement composition.

18. A composition, according to claim 12, wherein the stabilizing composition for ubiquinol supplement comprises ascorbyl palmitate, propylene glycol and carboxymethylcellulose.

* * * * *